(12) United States Patent
Hwang et al.

(10) Patent No.: US 8,551,071 B2
(45) Date of Patent: Oct. 8, 2013

(54) GAS-PRESSURED MEDICATION DELIVERY DEVICE

(75) Inventors: Chorng-Fure Robin Hwang, Thousand Oaks, CA (US); David Moore, Oceanside, CA (US); John Zeis, San Marcos, CA (US)

(73) Assignee: Halozyme, Inc., San Diego, CA (US)

( * ) Notice: Subject to any disclaimer, the term of this patent is extended or adjusted under 35 U.S.C. 154(b) by 273 days.

(21) Appl. No.: 13/051,719

(22) Filed: Mar. 18, 2011

(65) Prior Publication Data
US 2011/0238037 A1 Sep. 29, 2011

Related U.S. Application Data

(60) Provisional application No. 61/315,893, filed on Mar. 19, 2010.

(51) Int. Cl.
*A61M 31/00* (2006.01)
*A61M 1/00* (2006.01)
*A61M 5/20* (2006.01)

(52) U.S. Cl.
USPC ............................ 604/506; 604/146; 604/156

(58) Field of Classification Search
USPC ............. 604/156, 30, 65, 131, 132, 140, 141, 604/145–147, 31, 66–71, 118, 151, 153, 604/246, 500, 506
See application file for complete search history.

(56) References Cited

U.S. PATENT DOCUMENTS

| 2,665,689 | A | | 1/1954 | Butler | |
|---|---|---|---|---|---|
| 3,064,648 | A | | 11/1962 | Bujan | |
| 3,683,911 | A | | 8/1972 | McCormick | |
| 3,700,360 | A | * | 10/1972 | Shaddock | 417/404 |
| 3,964,481 | A | * | 6/1976 | Gourlandt et al. | 604/152 |
| 4,040,427 | A | | 8/1977 | Winnie | |
| 4,108,176 | A | * | 8/1978 | Walden | 604/144 |
| 4,235,234 | A | | 11/1980 | Whitney et al. | |
| 4,319,609 | A | | 3/1982 | Debrus | |
| 4,380,234 | A | | 4/1983 | Kamen | |
| 4,491,154 | A | | 1/1985 | Peters | |
| 4,498,843 | A | | 2/1985 | Schneider et al. | |
| 4,579,120 | A | | 4/1986 | MacGregor | |

(Continued)

OTHER PUBLICATIONS

International Search Report and Written Opinion for corresponding PCT Application No. PCT/US2011/029030, dated May 12, 2011, 14pp.

*Primary Examiner* — Kevin C Sirmons
*Assistant Examiner* — William Carpenter
(74) *Attorney, Agent, or Firm* — Christie, Parker & Hale, LLP

(57) ABSTRACT

The present invention relates to medical devices and particularly to a medication delivery device for self-injection of a medication, or for healthcare professionals to administer a medication. In one embodiment, a medication delivery device utilizes a source of gas pressure to deploy a needle, deliver a desired amount of medication through the needle, and retract the needle for disposal. Fluid flow paths from the source of gas pressure communicate the gas pressure to the needle and to the medication in order to accomplish these steps. In one embodiment, a valve is positioned to open and close the flow of the pressurized gas to the needle and the flow of the medication to the needle, so that the valve can be operated to deploy the needle and deliver the medication through the needle when the user is ready for the injection. The valve can also be operated to retract the needle when the dose is complete.

20 Claims, 10 Drawing Sheets

(56) References Cited

U.S. PATENT DOCUMENTS

| | | | |
|---|---|---|---|
| 4,645,495 A | 2/1987 | Vaillancourt | |
| 4,755,173 A | 7/1988 | Konopka et al. | |
| 4,886,499 A * | 12/1989 | Cirelli et al. | 604/131 |
| 5,312,353 A | 5/1994 | Boggess et al. | |
| 5,370,614 A | 12/1994 | Amundson et al. | |
| 5,616,132 A | 4/1997 | Newman | |
| 5,700,245 A | 12/1997 | Sancoff et al. | |
| 5,785,688 A * | 7/1998 | Joshi et al. | 604/141 |
| 5,792,099 A | 8/1998 | DeCamp et al. | |
| 5,858,001 A | 1/1999 | Tsals et al. | |
| 5,858,005 A | 1/1999 | Kriesel | |
| 5,860,957 A * | 1/1999 | Jacobsen et al. | 604/156 |
| 6,017,328 A | 1/2000 | Fischell et al. | |
| 6,045,534 A * | 4/2000 | Jacobsen et al. | 604/156 |
| 6,165,155 A * | 12/2000 | Jacobsen et al. | 604/156 |
| 6,288,348 B1 | 9/2001 | Eberts et al. | |
| 6,293,925 B1 | 9/2001 | Safabash et al. | |
| 6,485,461 B1 * | 11/2002 | Mason et al. | 604/132 |
| 6,500,150 B1 | 12/2002 | Gross et al. | |
| 6,565,535 B2 | 5/2003 | Zaias et al. | |
| 6,582,393 B2 | 6/2003 | Sage, Jr. | |
| 6,595,956 B1 | 7/2003 | Gross et al. | |
| 6,699,218 B2 | 3/2004 | Flaherty et al. | |
| 6,824,529 B2 | 11/2004 | Gross et al. | |
| 6,843,782 B2 | 1/2005 | Gross et al. | |
| 6,986,758 B2 | 1/2006 | Schiffmann | |
| 7,329,239 B2 | 2/2008 | Safabash et al. | |
| 7,384,413 B2 | 6/2008 | Gross et al. | |
| 7,407,491 B2 | 8/2008 | Fangrow, Jr. | |
| 7,416,540 B2 * | 8/2008 | Edwards et al. | 604/144 |
| 7,637,891 B2 | 12/2009 | Wall | |
| 7,648,482 B2 | 1/2010 | Edwards et al. | |
| 7,842,010 B2 * | 11/2010 | Bonnette et al. | 604/131 |
| 8,021,357 B2 * | 9/2011 | Tanaka et al. | 604/890.1 |
| 8,105,280 B2 * | 1/2012 | Iddan et al. | 604/131 |
| 2003/0152637 A1 | 8/2003 | Chasin et al. | |
| 2004/0138622 A1 | 7/2004 | Palasis | |
| 2005/0059926 A1 | 3/2005 | Sage, Jr. et al. | |
| 2005/0165359 A1 | 7/2005 | Dalton | |
| 2005/0197633 A1 | 9/2005 | Schwartz et al. | |
| 2005/0260186 A1 | 11/2005 | Bookbinder et al. | |
| 2005/0288651 A1 | 12/2005 | VanTassel et al. | |
| 2007/0134228 A1 | 6/2007 | Stern et al. | |
| 2008/0234630 A1 | 9/2008 | Iddan et al. | |

* cited by examiner

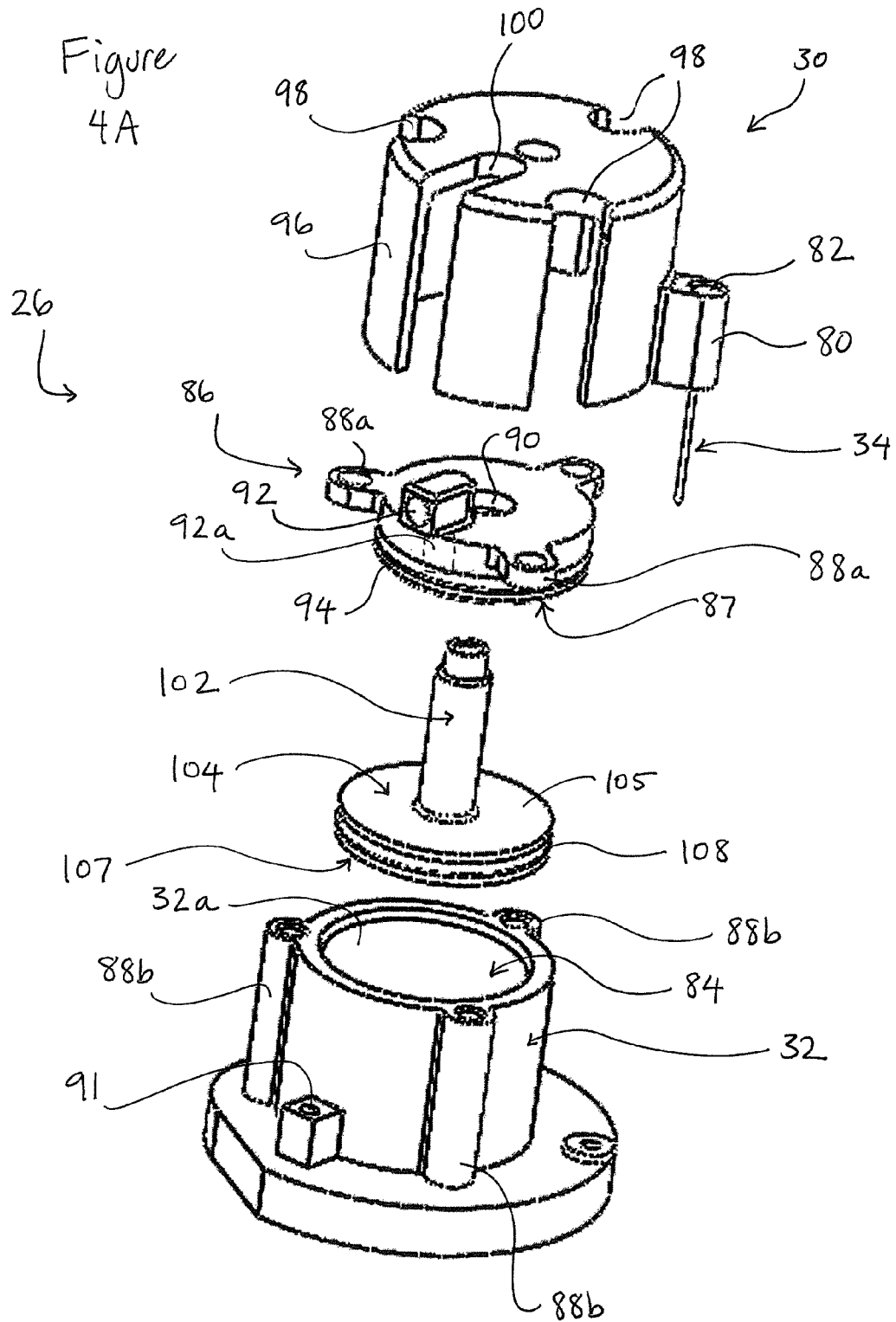

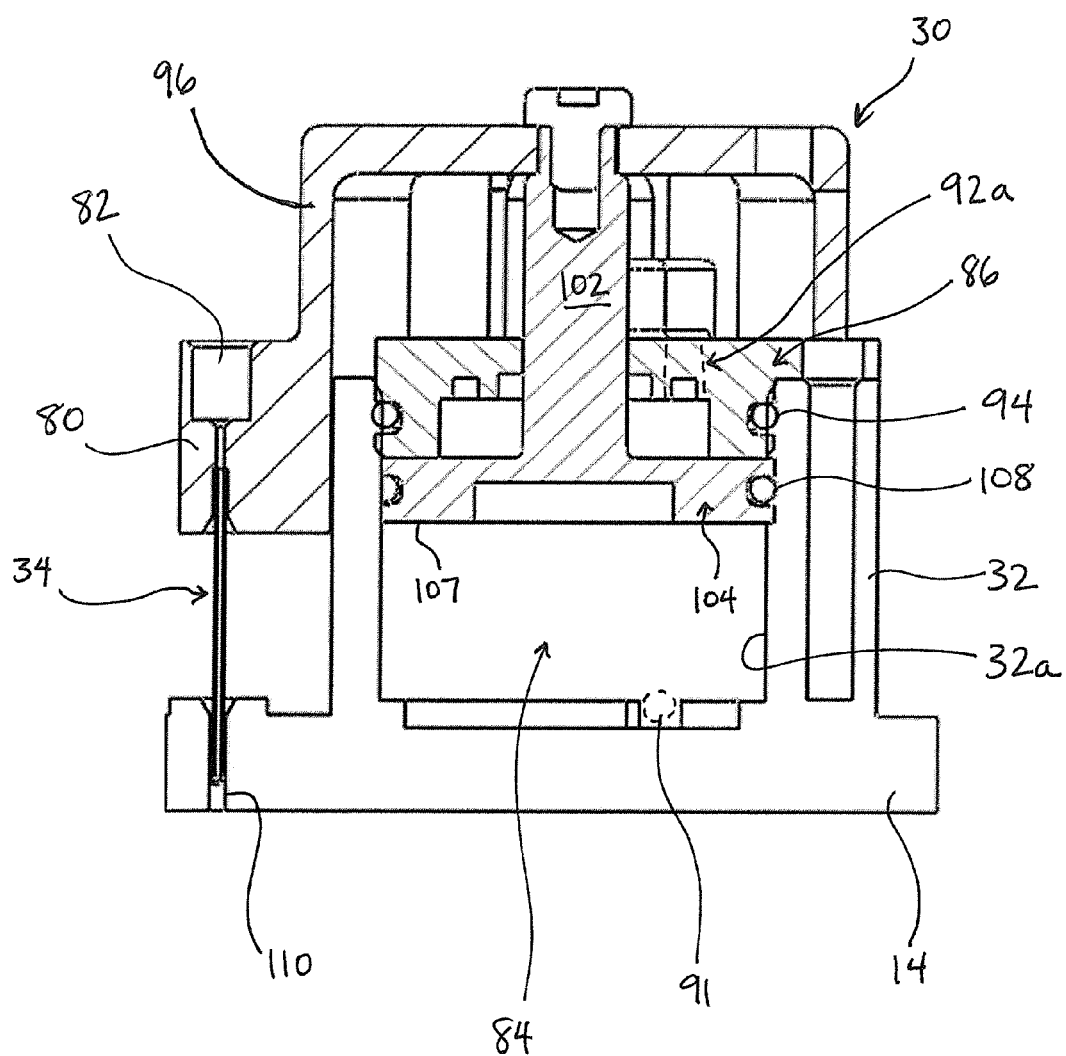

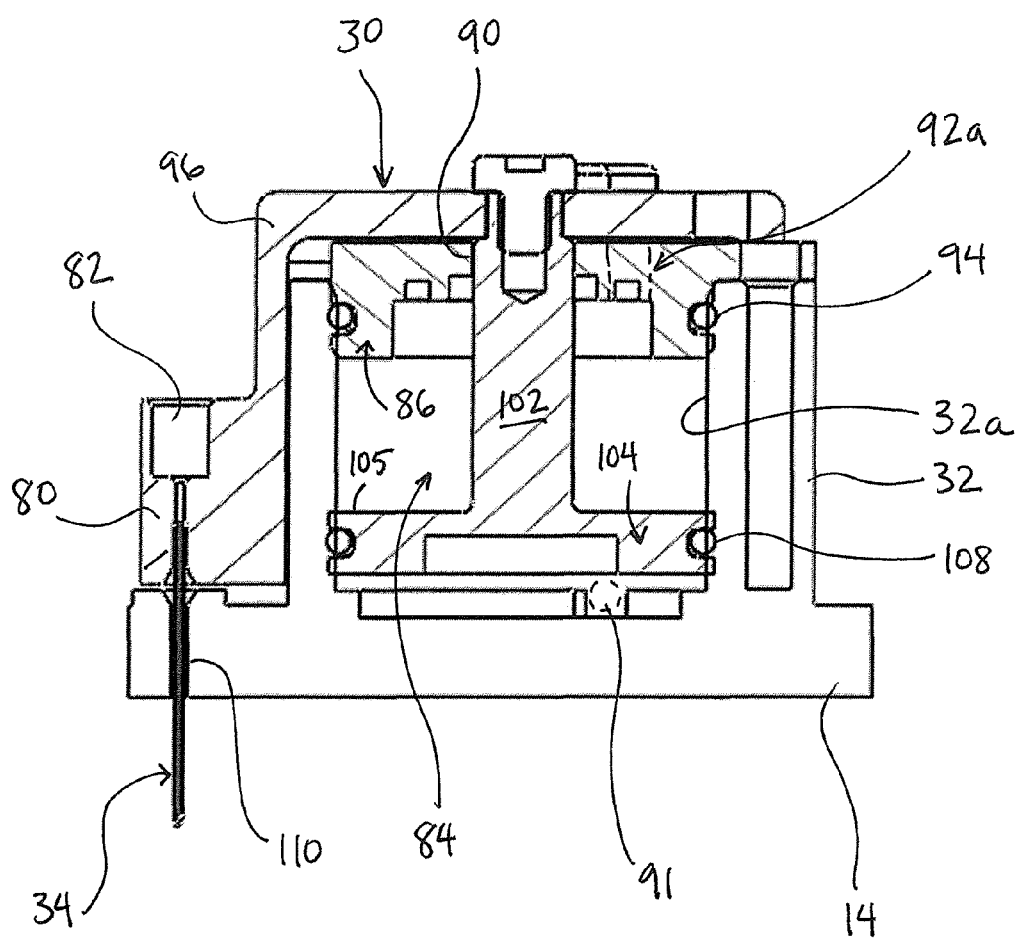

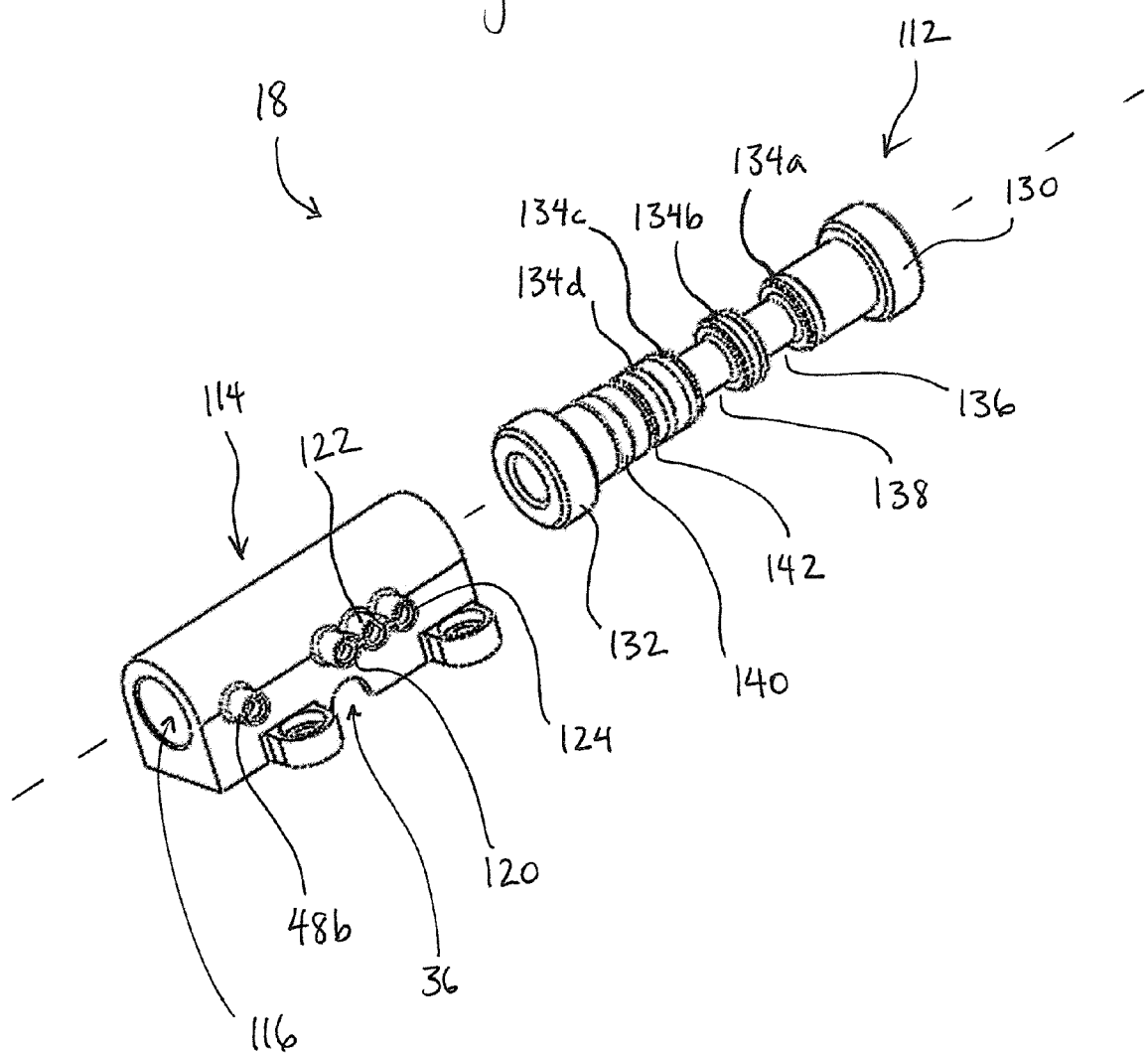

GAS-PRESSURED MEDICATION DELIVERY DEVICE

CROSS-REFERENCE TO RELATED APPLICATION(S)

This application claims priority to and the benefit of U.S. Provisional Application No. 61/315,893, filed on Mar. 19, 2010, the entire content of which is incorporated herein by reference.

FIELD OF THE INVENTION

The present invention relates to medical devices and particularly to a medication delivery device for self-injection of a medication.

BACKGROUND

In various situations, it is desirable or even medically necessary for patients to self-administer medication away from a doctor's office or professional medical setting. Such medication may take the form of a liquid or reconstitutable liquid drug administered by sub-cutaneous or intramuscular needle injection. Various medical devices have been developed to enable patients to perform these self-injections without the assistance of a medical professional.

An example of an injection device is shown in U.S. Pat. No. 5,616,132. This patent discloses a portable medicant injection device with a needle that moves when pressurized gas is released into a housing. The user presses downwardly on the device to release the gas, which forces a diaphragm downwardly, carrying the needle with it. The gas pressure also moves a plunger downwardly to force the medication through the needle. After the gas escapes, the diaphragm returns to its normal position, withdrawing the needle.

Many drug delivery devices utilize stored energy to insert the needle into the patient and deliver the medication. This energy can be stored in the form of material resiliency, compressed springs, magnets, batteries, pressurized gas, or chemical reaction. A combination of these components may be utilized, along with other mechanical components such as ratchets, levers, and hinges. These various moving parts and energy sources can be complicated for the patient to use.

Accordingly, there is still a need for a medication delivery device that is simple to use and enables the patient to safely inject a needle, deliver a desired dose of medication, and dispose of the used needle without professional medical assistance.

SUMMARY OF THE INVENTION

The present invention relates to medical devices and particularly to a medication delivery device for self-injection of a medication, or for healthcare professionals to administer a medication. In one embodiment, a medication delivery device utilizes a source of gas pressure to deploy a needle, deliver a desired amount of medication through the needle, and retract the needle for disposal. Fluid flow paths from the source of gas pressure communicate the gas pressure to the needle and to the medication in order to accomplish these steps. In another embodiment, a valve is positioned to open and close the flow of the pressurized gas to the needle and the flow of the medication to the needle, so that the valve can be operated to deploy the needle and deliver the medication through the needle when the user is ready for the injection. The valve can also be operated to retract the needle when the dose is complete.

BRIEF DESCRIPTION OF THE DRAWINGS

FIG. 4A is an exploded perspective view of a piston and needle assembly according to an embodiment of the invention.

FIG. 4B is a cross-sectional view of the piston and needle assembly of FIG. 4A in a retracted position.

FIG. 4C is a cross-sectional view of the piston and needle assembly of FIG. 4A in a deployed position.

FIG. 5 is an exploded view of a valve according to an embodiment of the invention.

DETAILED DESCRIPTION OF THE INVENTION

The present invention relates to medical devices and particularly to a medication delivery device for self-injection of a medication, or for healthcare professionals to administer a medication. In one embodiment, a medication delivery device utilizes a source of gas pressure to deploy a needle, deliver a desired amount of medication through the needle, and retract the needle for disposal. Fluid flow paths from the source of gas pressure communicate the gas pressure to the needle and to the medication in order to accomplish these steps. In one embodiment, a valve is positioned to open and close the flow of the pressurized gas to the needle and the flow of the medication to the needle, so that the valve can be operated to deploy the needle and deliver the medication through the needle when the user is ready for the injection. The valve can also be operated to retract the needle when the dose is complete.

Figure 1:
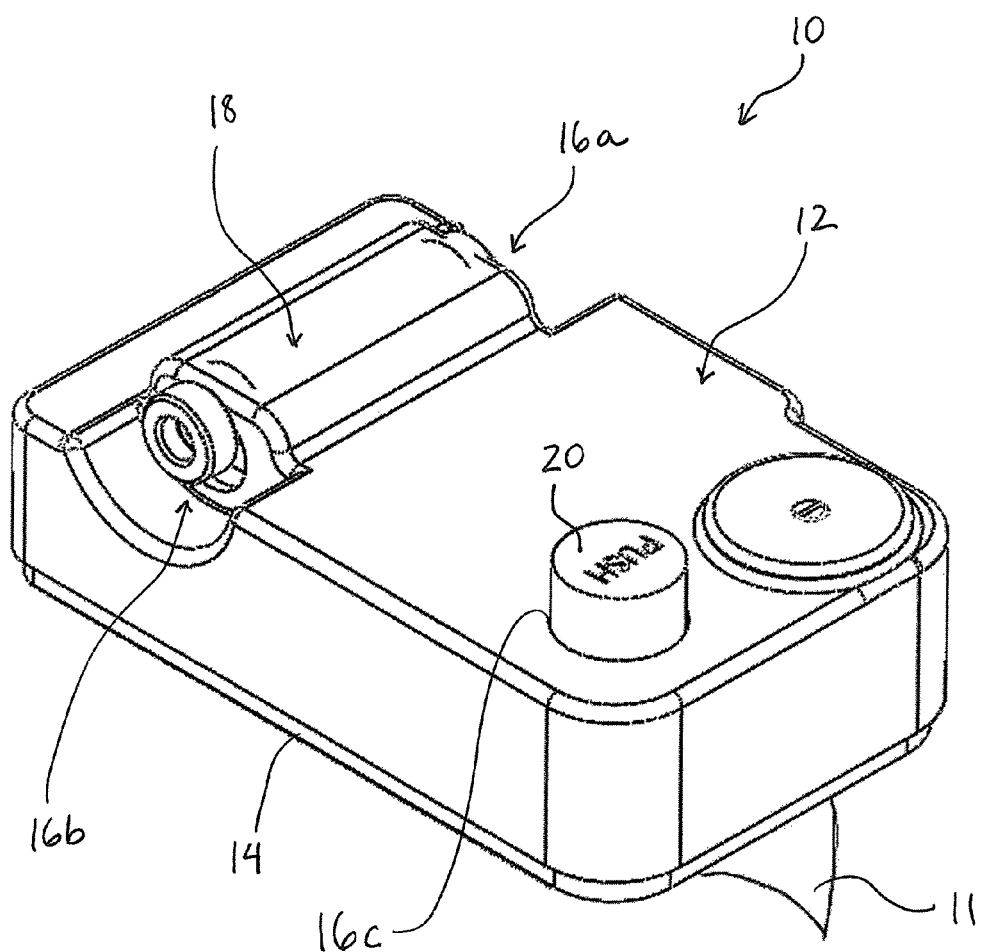
FIG. 1 is a top perspective view of a medication delivery device according to an embodiment of the invention.

An embodiment of a medication delivery device 10 is shown in FIG. 1. The device includes a cover 12 that slidably fits over a base 14. The various active components of the device are mounted to the base and enclosed under the cover. In the embodiment shown, the cover 12 includes three openings 16a, 16b, 16c. The first two openings 16a, 16b are access windows for operating the valve 18, which will be described in further detail below. The third opening 16c allows an activation button 20 to pass through the cover 12 and extend upwardly for the patient's use.

Figure 2:
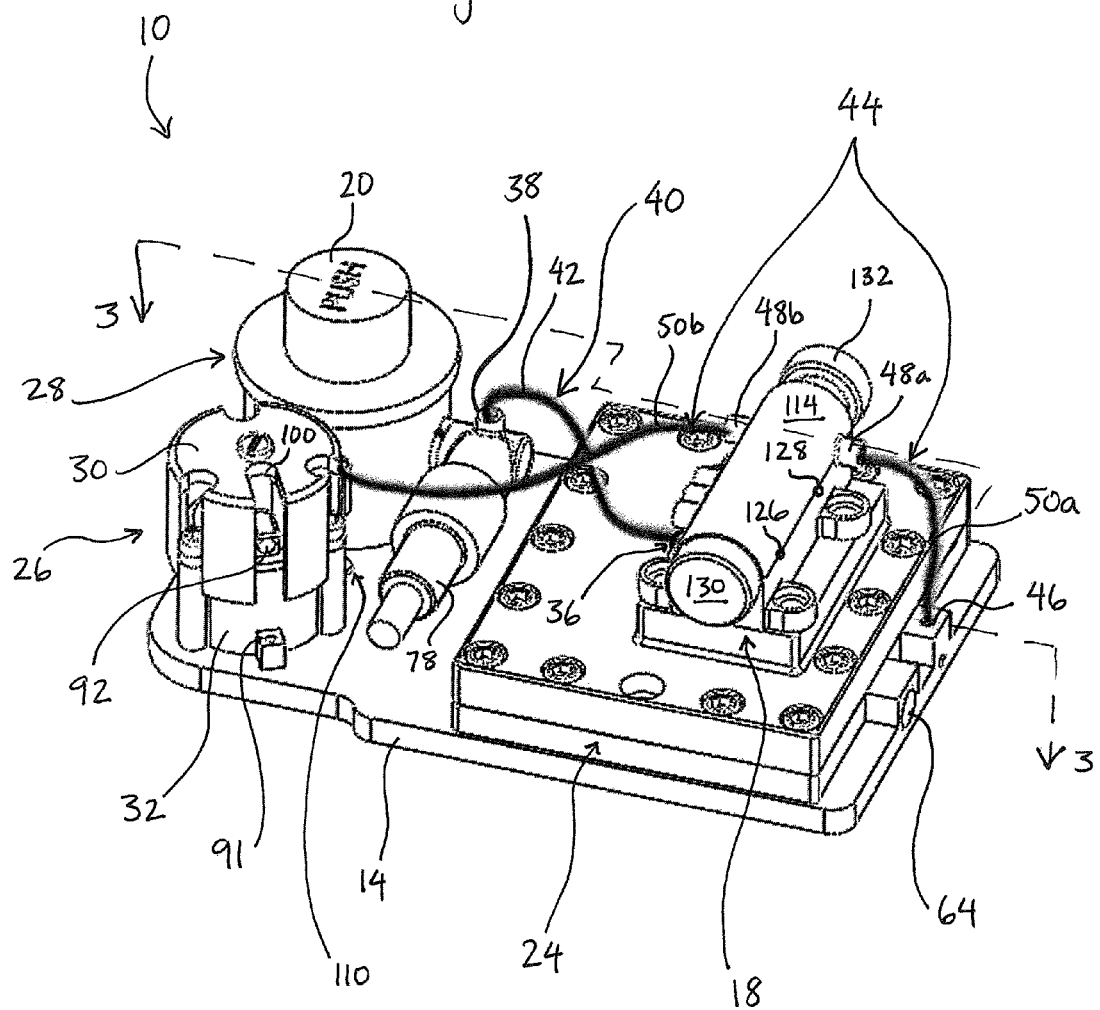
FIG. 2 is a front perspective view of the device of FIG. 1, with the cover removed.

The device 10 with the cover 12 removed is shown in FIG. 2. Mounted to the base 14 are the main components of the drug delivery device, including the valve 18, a medication reservoir 24, a piston assembly 26, and a power cell such as a pressure housing 28. The medication reservoir 24 includes a liquid medication, such as a liquid drug or a solution or suspension of a solid drug.

The piston assembly 26 includes a piston 30 that slides up and down over a piston housing 32. The piston 30 is connected to a needle 34 (shown in FIG. 3). The piston 30 moves up and down to deploy and retract the needle. The pressure housing 28 includes a source of gas pressure (described in further detail below) which is routed through the device 10 to deploy the needle and deliver the medication. The valve 18 controls the flow of gas pressure and medication to the piston assembly 26.

The device 10 has several flow paths for fluid flow within the device, including flow of gas pressure and medication. These flow paths are introduced here and described in detail below. A first pressure flow path 40 extends from the pressure housing 28 to the medication reservoir 24, to apply pressure to the liquid medication to cause it to flow to the needle. A medication flow path 44 extends from the medication reservoir 24, through the valve 18 and to the needle 34, so that medication flows through the needle into the user's skin. A second pressure flow path 150 (see FIG. 6) extends from the pressure housing 28 to a downwardly-facing surface of the piston 30. Gas pressure from this path raises the piston 30 into the retracted position, retracting the needle inside the device 10. A third pressure flow path 152 (see FIG. 7) extends from the pressure housing 28 to an upwardly-facing surface of the piston 30. Gas pressure from this path pushes the piston down into the deployed position, with the needle extending from the device 10 to be inserted into the user's skin. The valve 18 is moved to alternate between opening the second flow path and closing the third flow path (to raise the piston) and opening the third flow path and closing the second flow path (to lower the piston). When either the second or third flow path is closed, a corresponding vent path is opened to vent the opposite side of the piston. This allows the piston to be moved up and down by the gas pressure when the user operates the valve.

With this introduction, the specific components of the device 10 will now be described. As shown in FIG. 2, the pressure housing includes an outlet 38, through which the gas pressure from the pressure housing flows to the various components in the device. The medication reservoir 24 includes an inlet 36 for receiving this gas pressure. The first pressure flow path 40 connects the outlet 38 of the pressure housing 28 to the inlet 36 of the medication reservoir 24. The flow path 40 fluidically couples the pressure housing 28 to the medication reservoir 24, meaning that a path for fluid communication exists between the pressure housing 28 and the medication reservoir 24. In the embodiment shown, the first pressure flow path 40 includes a tube or conduit 42 that is connected at one end to the outlet 38 of the pressure housing 28 and at the opposite end to the inlet 36 of the medication reservoir 24. When the user presses the activation button 20 and builds gas pressure in the pressure housing 24 (as described in further detail below), the gas pressure flows through the tube 42 along the first pressure flow path 40 through the inlet 36 and into the medication reservoir 24, where the gas exerts pressure on the liquid medication to cause it to flow to the needle 34.

Figure 3:
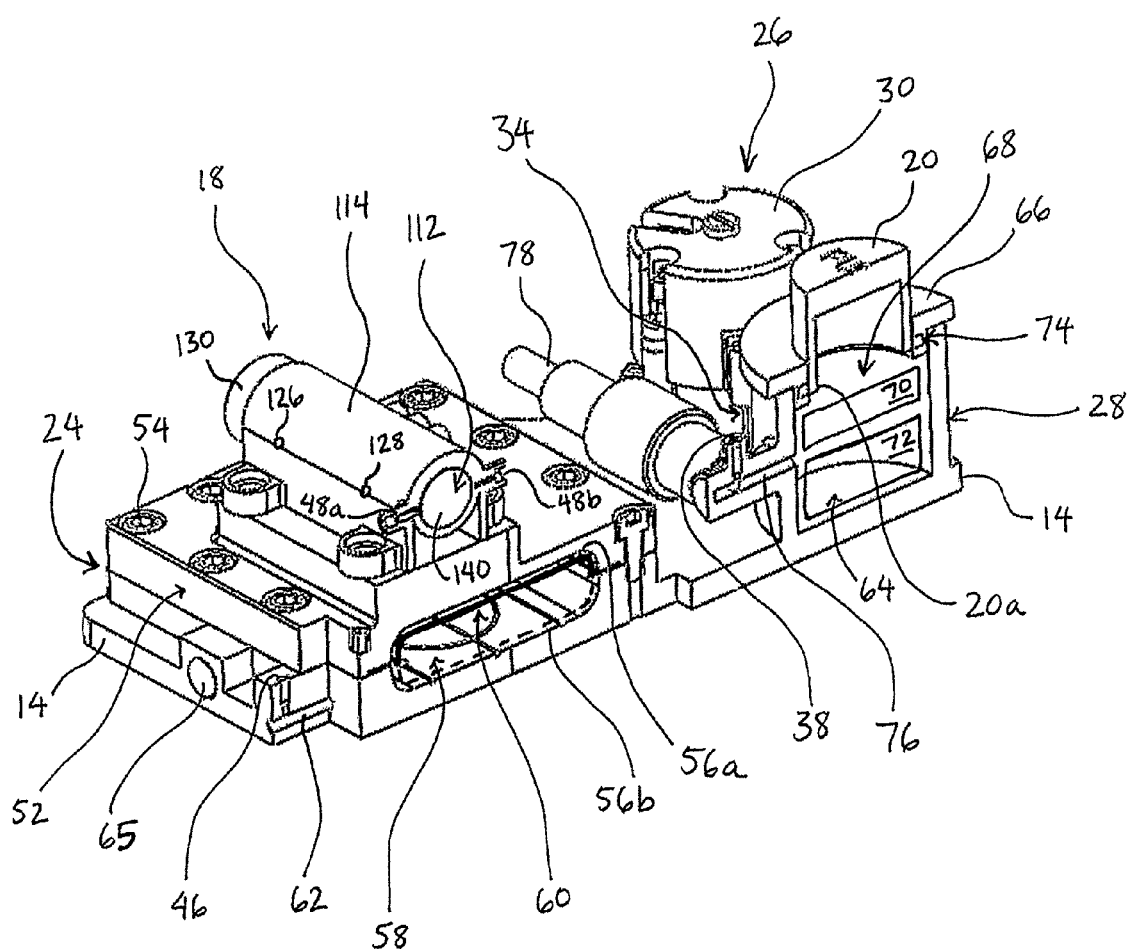
FIG. 3 is a rear perspective view of the device of FIG. 1, taken along the cross-section 3-3 in FIG. 2.

The gas pressure in the first pressure flow path 40 pushes the medication in the medication reservoir 24 and causes it to flow from the medication reservoir 24 through an outlet 46 and through the medication flow path 44 to the needle 34 (see FIG. 3). The medication flow path 44 fluidically couples the medication reservoir 24 to the needle 34, through the valve 18. The medication flow path 44 passes into an inlet 48a on a first side of the valve 18 and out of an outlet 48b on the opposite side of the valve 18. The valve itself is moved to allow or block flow of the medication through the valve, between this inlet 48a and outlet 48b. The flow path 44 includes a tube or conduit, which is divided into a first tube portion 50a extending from the medication outlet 46 to the valve inlet 48a, and a second tube portion 50b extending from the valve outlet 48b to the needle 34.

Referring now to FIG. 3, the medication reservoir 24 includes a lid 52 attached to the base 14 by fasteners such as screws 54. The lid 52 and the base 14 each include a matching depression 56a, 56b, respectively, that face each other when the lid 52 is attached. The depressions form a cavity 58 where the liquid medication is stored. The medication may be stored directly within the cavity 58, or it may be included in a sealed bag within the cavity 58. In either case, the medication reservoir 24 may include a flexible membrane 60 arched across the cavity 58 and matching the shape of the depression 56a. When the gas pressure from the pressure housing 28 flows through the first pressure flow path 40 to the medication reservoir 24, the gas pressure pushes on this membrane 60, which flexes downwardly and pushes on the medication in the cavity 58. The membrane 60 continues to flex downwardly as the medication flows from the cavity 58, until the membrane 60 reaches its mirror-image shape on the bottom of the cavity 58, along depression 56b, as shown in dotted lines in FIG. 3. In this position the membrane 60 matches the depression 56b so that no medication (or only a small trace amount) remains in the reservoir 24. The membrane 60 may be made of a flexible multilayer polymeric film.

When the medication flows from the cavity 58, it flows through an exit flow path 62 to the outlet 46. The exit flow path 62 is formed as a channel in a raised portion of the base 14, connecting the depression 56b to the outlet 46. From there the medication flows along the medication flow path 44 (shown in FIG. 2)—through the tube portion 50a, through the valve 18, and through the tube portion 50b to the needle 34, as described before.

Still referring to FIG. 3, the medication reservoir 24 also includes a fill port or septum 65 through which liquid medication can be inserted by needle injection into the cavity 58. The cavity 58 can be pre-filled with medication, or the medication can be inserted into the cavity through the fill port 65. The fill port 65 can also be used to inject a diluent into the cavity 58 to create a solution or suspension with a solid drug stored in the cavity 58. The fill port 65 is formed in a raised portion of the base 14 and is fluidically coupled to the depression 56b and into the cavity 58.

Turning now to the pressure housing 28, as shown in FIG. 3 the pressure housing 28 includes a reaction chamber 64 enclosed by a lid 66. The activation button 20 extends upwardly from the lid 66. The reaction chamber 64 includes a source of gas pressure 68. In the embodiment shown, the source of gas pressure 68 includes two chemical components 70, 72 that generate gas as a byproduct when the two components react. In one embodiment, the first component 70 is calcium carbonate and the second component 72 is citric acid. When these two components contact each other, they undergo a chemical reaction that generates carbon dioxide. This generation of carbon dioxide builds gas pressure within the reaction chamber 64.

The two reactants 70, 72 are stored separately from each other inside the reactant chamber 64, beneath the lid 66 and the activation button 20. Before the user is ready to operate the device, the reactants remain separated and no gas pressure is generated. The first pressure flow path 40 (see FIG. 2) from the pressure housing 28 to the medication reservoir 24 and the second and third pressure flow paths 150, 152 (see FIGS. 6-7) from the pressure housing 28 to the piston assembly 26 are not pressurized, as no gas pressure has been generated or released.

In order to operate the device and release the gas pressure, the user presses the activation button 20. The activation button 20 is connected to the lid 66 via a frangible connection 74. When the activation button 20 is pressed, the connection 74 is broken and the button 20 moves downwardly into the reactant chamber 64. A lower end 20a of the button 20 contacts the first reactant 70 and breaks a seal or otherwise moves the first reactant 70 into contact with the second reactant 72, initiating the chemical reaction and the generation of gas pressure. When the reactants are calcium carbonate and citric acid, the calcium carbonate may be stored as the first reactant 70 above the citric acid 72, so that the activation button 20 pushes the calcium carbonate 70 down into the liquid reservoir of citric acid 72. The calcium carbonate 70 can be provided in the form of a solid tablet, a powder, or a combination of a solid tablet and powder. These reactants can be packaged and stored within the pressure housing 28 in other ways as well. For example, the citric acid may be stored above the calcium carbonate, and the button 20 may rupture a seal to allow the citric acid to flow down over the calcium carbonate.

In one embodiment, the gas pressure generated by the reactants 70, 72 is sufficient to drive flow of the medication for a prolonged duration, to deliver a large volume sub-cutaneous injection. The volume of medication delivered by the device into the user's skin can vary from 1 mL to 300 mL depending on the situation. In one embodiment the volume of medication is approximately 10 mL. The source of gas pressure delivers a rapid burst of pressure, to inject the needle and cause the medication to flow through the needle for the duration of the injection until the dose is complete. In one embodiment, the pressure delivered by the source of gas pressure is approximately 20 psi at the time of activation, and falls to about 12 psi at the time of completion of the dose. The delivery time can vary from a few seconds to 10 minutes. In one embodiment, approximately 24 psi of pressure is generated within 5 seconds of activation of the pressure source, and the resulting medication flow rate is approximately 0.5 mL per second through a 27 gauge needle that is 1/2 inches in length. The device can be designed to deliver medication at flow rates ranging from 0.5 mL/second to 0.5 mL/minute.

The gas pressure builds inside the reactant chamber 64 and flows through an outlet path 76 which fluidically couples the reactant chamber 64 to the pressure outlet 38. From there, the gas flows through the first pressure flow path 40 (see FIG. 2) and through either the second or third pressure flow paths 150, 152 (see FIGS. 6-7) to deploy or raise the piston and to cause the liquid medication to flow to the needle (as described in further detail below). The path 76 also fluidically couples the reactant chamber 64 to a pressure relief valve 78. This pressure relief valve 78 is a safety feature that vents the gas within the chamber 64 in the case of over-pressurization.

As just described, the pressure housing 28 includes a source 68 of gas pressure that is activated by the user to cause gas to flow through the first pressure flow path 40 to the medication reservoir and through the second or third flow paths 150, 152 to the piston assembly 26. The piston assembly 26 is now described in reference to FIGS. 4A-4C. The piston assembly 26 includes the piston 30 that is movable over the piston housing 32. The piston 30 includes a hub 80 that is attached to the needle 34. The hub 80 is rigidly attached to the piston 30 so that the needle 34 moves with the piston 30. The hub 80 also includes a fluid inlet 82 that is connected to the medication flow path 44 (shown in FIG. 2), allowing medication to flow from the medication flow path 44 through the inlet 82 to the needle 34. The needle 34 itself is a hollow needle with a pointed distal end and a lumen through the needle for the flow of medication to the user. The distal end of the needle may be beveled.

The piston housing 32 is cylindrical in shape and includes a hollow interior chamber 84 with an inside surface 32a. The chamber 84 is closed on the lower end by the base 14 of the device 10, and on the upper end by a lid 86 (see FIGS. 4B-4C). The lid 86 and the piston housing 32 include matching wings or extensions 88a, 88b (respectively) that align when the lid 86 is placed onto the piston housing 32. Screws or other fasteners pass through the wings 88a into the wings 88b to attach the lid 86 to the piston housing 32. The lid 86 includes a central opening 90 for passage of the piston 30, to allow the piston 30 to move up and down. Lastly, the lid 86 includes an o-ring or other seal 94 that contacts the inside surface 32a of the piston housing 32 when the lid is attached to the housing, as shown in FIGS. 4B-4C. When the lid 86 is attached to the piston housing 32 via the wings 88a, 88b, the o-ring 94 creates an airtight seal at the top of the interior chamber 84. This seal contains the gas pressure that is routed to this interior chamber 84 to move the piston 30 up and down, as described in further detail below.

The piston 30 includes an outer shell 96, a post 102, and a plate 104. The plate 104 has a top, upwardly facing surface 105 and a bottom, downwardly facing surface 107. The shell 96 is cylindrical and is shaped and sized to pass over the piston housing 32. The shell 96 includes cutouts 98 that align with and engage the wings 88a, 88b. The engagement of the wings 88a, 88b in the cutouts 98 allows the shell 96 to move vertically along the piston housing and prevents the shell 96 from rotating around the piston housing 32. The shell 96 also includes a separate cutout 100 which aligns with an inlet 91 at the base of the housing 32 (described below) and aligns with an inlet 92 on the lid 86, so that the shell 96 can move downwardly over these inlets (see for example FIG. 2).

The post 102 connects the shell 96 to the plate 104. The post 102 extends from the plate 104 through the opening 90 in the lid 86 and is firmly mounted to the shell 96, such as by adhering the post 102 to an underside of the shell 96 or securing the post 102 to the shell 96 by fasteners such as screws. The shell 96, post 102, and plate 104 move together, sliding up and down over the piston housing 32 with the post 102 sliding through the opening 90 in the lid 86. The plate 104 includes an o-ring or other seal 108 that seals against the inside surface 32a of the base 32, inside the chamber 84. This o-ring 108 creates an airtight seal inside the housing 32 to contain gas pressure from the pressure housing, as described further below.

The piston 30 moves between two positions, as shown in FIGS. 4B and 4C. The movement of the piston 30 is caused by air flow through two separate inlets into the chamber 84. A first inlet 91 is located at the bottom of the housing 32, below the lid 86 and below the plate 104. A second inlet is located at the top of the lid 86 and connects to a passage 92a through the lid 86 into the chamber 84 above the top surface 105 of the plate 104. Thus, the lower inlet 91 leads to the chamber 84 below the bottom surface 107 of plate 104, and the upper inlet 92 leads to the chamber 84 above the top surface 105 of the plate 104.

The lower inlet 91 fluidically couples the second pressure flow path 150 to the chamber 84 below the plate 104, so that gas pressure flowing through this path enters the chamber 84 and pushes on the bottom, downwardly facing surface 107 of the plate 104 to raise the piston 30 into the retracted position, as shown in FIG. 4B. The upper inlet 92 fluidically couples the third pressure flow path 152 to the chamber 84 above the plate 104, so that gas pressure flowing through this path enters the chamber 84 and pushes on the top, upwardly facing surface 105 of the plate 104 to push the piston down into the deployed position, as shown in FIG. 4C.

In the retracted position of FIG. 4B, the needle 34 is contained within the device 10, above the base 14 and inside the cover 12. The plate 104 is raised to the lid 86. Air pressure in the chamber 84 below the plate 104 retains the piston 30 in this retracted position. This air pressure is sealed by the o-ring 108 on the plate 104.

In the deployed position of FIG. 4C, the needle 34 extends through an opening 110 in the base 14, extending out of the device 10 and into the user's skin. Air pressure in the chamber 84 above the plate 104 retains the piston 30 in this deployed position. This air pressure is sealed between the o-rings 94 and 108 on the lid 86 and plate 104, respectively. The piston plate 104 is near the bottom of the housing 32, but above the lower inlet 91, so that the o-ring seal 108 remains above the inlet 91 and prevents any gas leakage through the inlet 91. The shell 96 rests on the lid 86, preventing any further downward travel of the piston 30. The height of the shell 96 determines the stroke of travel of the needle 34, and thus determine the depth of penetration of the needle into the user's skin. In one embodiment, the depth of injection is 6-9 mm, and the height of the piston is slightly larger than that depth in order to move the needle from its retracted position above the base 14 through the base 14 and to the desired depth of injection. Additional information regarding the appropriate depths for subcutaneous needle injection can be found in the figures and description of U.S. Pat. No. 6,544,238.

As indicated by FIGS. 4B and 4C, alternating air pressure between the lower inlet 91 and the upper inlet 92 causes the piston 30 to move up and down. When one inlet is pressurized, the other inlet is vented, so that the piston 30 can travel through the chamber 84. The gas pressure paths 150, 152 and vent paths 154, 156 are described in further detail below in connection with FIGS. 6-7.

The flow of gas pressure to the piston assembly 26 to raise and lower the piston 30 is controlled by the valve 18, which is shown in FIG. 5. The valve 18 interrupts the medication flow path from the medication reservoir to the needle and interrupts the second and third pressure flow paths from the pressure housing 28 to the piston assembly 26, in order to control the insertion of the needle and the delivery of medication through the needle. In the embodiment shown, the valve 18 is a spool-type valve with a spool 112 that reciprocates within a valve housing 114. The valve housing 114 includes a central channel 116 through which the spool 112 extends.

The spool 112 and housing 114 include openings, seals, and grooves that are positioned to allow or block gas pressure and medication to the piston assembly 26. The spool 112 is moved back and forth within the housing 114 between two different positions (a start position and a stop position) in order to open and close various flow paths through the valve. By sliding the spool in one direction or the other within the channel 116, the grooves and seals on the spool 112 align with openings in the housing 114 to open and close the flow paths to the piston assembly 26.

In the embodiment of FIG. 5, the openings on the housing 114 include two openings for the flow of medication and three openings and two vents for the flow of gas pressure. The two openings for the medication flow are the inlet 48a and outlet 48b described above in reference to FIG. 2. The inlet and outlet 48a, 48b pass through the valve housing 114 to the channel 116. The medication flows from the medication reservoir 24 through the tube 50a into the inlet 48a on the valve housing. The spool 112 then either allows or blocks further flow of the medication. The medication flow path 44 continues through the outlet 48b on the opposite side of the housing 114 and through the tube 50b to the needle 34.

The valve housing 114 also includes three openings 120, 122, and 124 for routing the flow of gas pressure from the pressure housing 28. These openings pass through the housing 114 to the channel 116. The openings are fluidically coupled to the first and second pressure flow paths 150, 152. On the opposite side of the housing 114 from these openings 120-124, two vent ports 126, 128 are provided (see FIG. 2) which pass through the housing 114 to the channel 116. These openings 120, 122, 124 and vent ports 126, 126 are alternatively opened or closed to each other by movement of the spool 112.

The spool 112 includes two opposite ends, the first end forming a start button 130 and the second opposite end forming a stop button 132. The user pushes on these opposite ends of the spool to operate the valve 18. Along the length of the spool are four spaced-apart o-rings 134a, 134b, 134c, 134d. Between the o-ring 134d and the stop button 132 is a wider liquid seal 140. Between the o-rings 134a and 134b and between the o-rings 134b and 134c are indentations 136, 138 (respectively) which form flow paths for the gas pressure. A groove 142 is included between the liquid seal 140 and the o-ring 134d.

Figure 6:
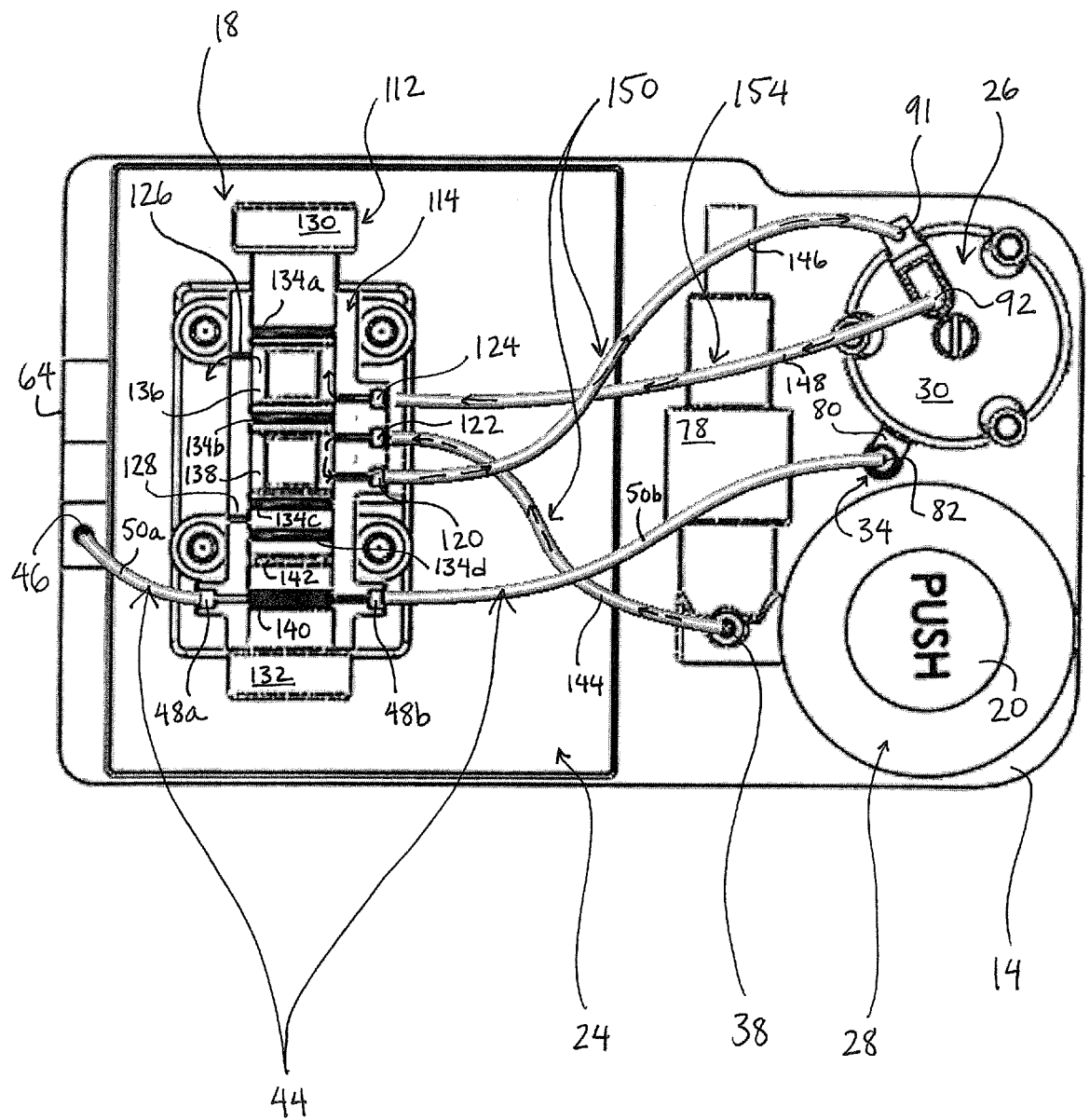
FIG. 6 is a top view of a medication delivery device according to an embodiment of the invention, with the cover removed and the valve shown in cross-section, for clarity, in a retracted position.
Figure 7:
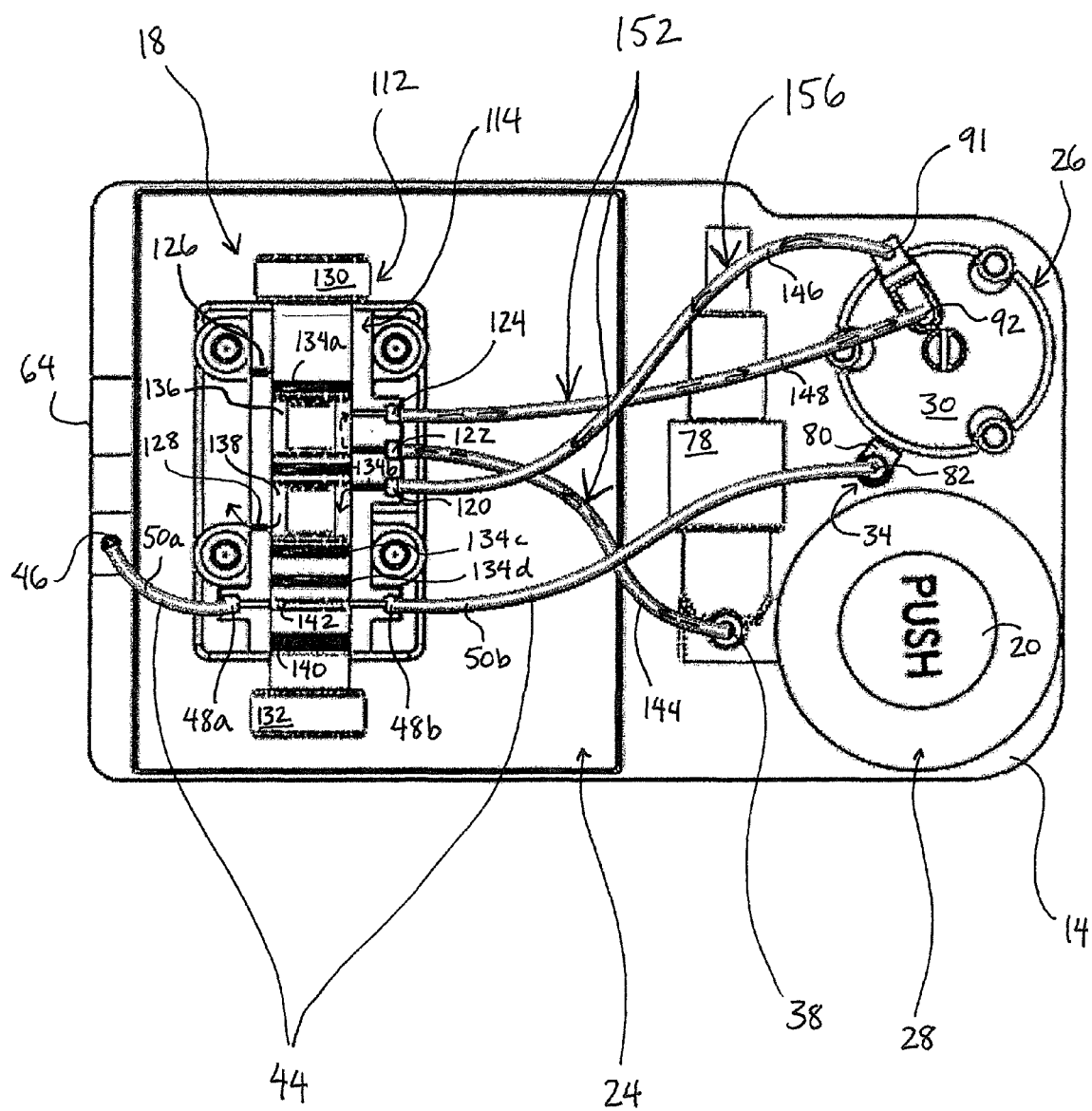
FIG. 7 is a top view of a medication delivery device of FIG. 6 in a deployed position.

These features on the spool 112 and housing 114 are shown in cross-section in FIGS. 6-7 to show operation of the valve 18 and the flow of liquid and gas through the valve in its start and stop positions. FIG. 6 shows the valve 18 in the stop position, with the stop button 132 on the spool 112 contacting the housing 114, and the start button 130 extending out of the housing and ready to be pressed. In this stopped position, the valve 18 prevents fluid flow through the medication flow path 44 to the needle. The valve 18 also opens the second pressure flow path 150 to the bottom of the piston 30 and closes the third pressure flow path 152 to the top of the piston 30. Additionally, the valve 18 opens the upper vent path 154 from the top of the piston to the vent port 126, and closes the lower vent path 156 from the bottom of the piston to the vent port 128. Each of these flow paths are described in detail below. In FIGS. 6 and 7, the first pressure flow path 40 (from the pressure housing 28 through tube 42 to the medication reservoir 24) is omitted for clarity (shown in FIG. 2).

Referring to FIG. 6, with the valve 18 in the stopped position, the liquid seal 140 blocks the medication flow path 44 between the inlet 48a and the outlet 48b on the valve housing 114. In this embodiment, the medication flow path 44 is larger in cross-sectional area than the various gas pressure flow paths, to overcome friction along the tubes and allow smooth flow of the liquid medication to the needle. As a result, the liquid seal 140 is wider than the o-rings 134a-d in order to fully seal the medication flow path 44. With the valve 18 in the stopped position, prior to use of the device by the user, the liquid medication may flow from the medication reservoir through tube 50a to the inlet 48a. However, with the valve in the stopped position as shown, the liquid seal 140 prevents any further flow of medication. The medication does not pass around this seal 140 and does not reach the tube 50b leading to the needle 34. The valve 18 thus prevents any premature delivery of medication to the needle.

Still referring to FIG. 6, in the stopped position, the valve 18 opens the second pressure flow path 150. This flow path 150 fluidically couples the pressure housing 28 to the piston assembly 26. Specifically, the flow path 150 connects at one end to the outlet 38 of the pressure housing and at the opposite end to the lower inlet 91 of the housing 32. Gas flow through this lower inlet 91 enters the chamber 84 below the plate 104 and presses on the downwardly facing surface 105 of the plate 104, thereby raising the plate and the piston into the retracted position. The flow path 150 includes a first tube 144 from the outlet 38 of the pressure housing 28 to the opening 122 in the valve housing 114, and a second tube 146 from the opening 120 in the valve housing 114 to the inlet 91. The flow path 150 passes through the first tube 144, through the opening 122 in the housing 114, through the indentation 138 in the spool 112, through the opening 120 in the housing 114, and through the second tube 146 into the inlet 91.

In the stopped position, the indentation 138 in the spool 112 aligns with the two openings 120, 122 in the housing 114 in order to open the second pressure flow path 150. The two tubes 144 and 146 are connected by this indentation 138 in the spool 112. The o-rings 134b and 134c on either side of the indentation 138 constrain the gas to flow from the first tube 144 into the second tube 146. The o-rings 134b and 134c prevent the gas from leaking through the valve 18 and escaping through any other path. Thus in this position, pressure is routed from the pressure housing 28 to the inlet 91 below the plate 104, to lift the piston 30. Flow through this pressure flow path 150 is indicated by dotted arrows in FIG. 6.

Still referring to FIG. 6, in the stopped position, the valve 18 also opens the upper vent path 154. This path 154 fluidically couples the upper inlet 92 (above the plate 104) to the vent port 126. This path 154 allows air above the plate 104 to be vented as the plate 104 moves upward due to the pressure below the plate 104 from the second pressure flow path 150. The upper vent path 154 includes a third tube 148 that connects the upper inlet 92 to the opening 124 in the valve housing 114. From there the vent path 154 passes through indentation 136 to the vent port 126. The vent port 126 opens to the surrounding air, below the cover 12 (see FIG. 1).

In the stopped position of the valve, the indentation 136 aligns with the opening 124 and the vent port 126 to open the upper vent path 154. The opening 124 and the vent port 126 are connected by this indentation 136 on the spool 112. The o-rings 134a, 134b on either side of the indentation 136 constrain the air in this path to flow from the tube 148 into the vent port 126. These o-rings prevent the air from leaking through the valve 18 and escaping through another path. Thus in this position, the air in the chamber 84 above the plate 104 passes through the upper vent path 154 and out the vent port 126. This path is shown by the solid arrows in FIG. 6.

Thus, the valve 18 in the stopped position of FIG. 6 closes the medication flow path 44 (via seal 140), opens the second pressure flow path 150 (via indentation 138), and opens the upper vent path 154 (via indentation 136). As a result, medication is prevented from flowing to the needle, and the piston 30 is raised into the retracted position.

FIG. 7 shows the valve 18 in the start position. The spool 112 has been moved in the direction from the start button 130 toward the stop button 132 (downwardly in the orientation of FIG. 7) until the start button 130 contacts the housing 114. The stop button 132 extends from the opposite end of the housing 114, ready to be pressed to stop the operation of the device. In this position, the spool 112 opens the medication flow path 44, closes the second pressure flow path 150, closes the upper vent path 154, opens the third pressure flow path 152, and opens the lower vent path 156. These flow paths are each described in detail below.

As shown in FIG. 7, in the start position, the groove 142 on the spool 112 between the liquid seal 140 and the o-ring 134d is aligned with the medication flow path 44, between the inlet 48a and outlet 48b on the valve housing 114. This alignment opens the medication flow path 44, as the liquid seal 140 no longer blocks flow between the inlet 48a and outlet 48b. When the pressure from the pressure housing 28 is generated, it flows through the first pressure flow path 40 (see FIG. 2) into the medication reservoir 24 and pushes on the flexible membrane 60 to push the liquid medication through the outlet 46 into the tube 50a. With the valve 18 in the start position, the liquid medication flows from the tube 50a through the inlet 48a, through the groove 142, through the outlet 48b, and through the tube 50b to the needle 34.

Additionally, when the valve 18 is moved to the start position, the second pressure flow path 150 (shown in FIG. 6) is closed. The o-ring 134b is positioned between the opening 122 and the opening 120 in the valve housing 114, thereby blocking air flow from the tube 144 to the tube 146. This o-ring 134b interrupts the flow path 150 by preventing gas pressure from the pressure housing 28 from flowing through the valve 18 to the tube 146 to the lower inlet 91. The indentation 138 that connected the two tubes 144, 146 and the two openings 122, 120 in the stopped position of FIG. 6 is no longer aligned with these openings. As a result the second pressure flow path 150 from the pressure housing 28 to the lower inlet 91 is closed.

Additionally, in FIG. 7, the upper vent path 154 is closed. The o-ring 134a is positioned between the opening 124 and the vent port 126. This o-ring 134a blocks air flow from the tube 148 to the vent port 126, thereby closing the upper vent path 154 (shown in FIG. 6). The indentation 136 that connects the opening 124 and the vent port 126 in the stopped position of the valve is no longer aligned with the vent port 126, so air cannot flow from the tube 146 to the vent port 126.

The valve 18 in FIG. 7 opens two additional flow paths. When the spool 112 translates from the stop position in FIG. 6 to the start position in FIG. 7, the indentation 136 moves into alignment with the tube 144 and the tube 148, thereby opening the third pressure flow path 152. The third pressure flow path fluidically couples the pressure housing 28 to the upper inlet 92 of the piston assembly 26. Specifically, gas pressure following the third pressure flow path 152 flows from the outlet port 38 of the pressure housing 28, through the tube 144, into the opening 122 of the housing 114, through the indentation 136, out of the opening 124 in the housing 114, and through the tube 148 to the upper inlet 92. This flow path is shown by the dotted arrows in FIG. 7. Gas pressure follows this path from the pressure housing 28 to the piston assembly 26, entering the chamber 84 through the inlet 92 and passage 92a, above the upwardly-facing surface 105 of the piston plate 104. The gas pushes down on this surface 105 of the piston plate 104, causing the piston 30 to move down into the deployed position (shown in FIG. 4C). The o-rings 134a, 134b on opposite sides of the indentation 136 constrain the flow of gas pressure from the tube 144 to the tube 148 and prevent the gas from leaking through the valve 18 and escaping through another path.

At the same time, the valve 18 opens the lower vent path 156 to vent the chamber 84 below the piston plate 104. The lower vent path 156 fluidically couples the lower inlet 91 to the vent port 128. Specifically, the lower vent path 156 passes from the lower inlet 91 through tube 146, into the opening 120 in the housing 114, and through the indentation 138, exiting through the vent port 128. This path 156 is shown in solid arrows in FIG. 7. The o-rings 134b and 134c constrain the flow of air through this flow path, providing a seal on either side of the indentation 138 to prevent leakage of the air through the valve 18.

As shown in FIGS. 6-7, the indentations 136 and 138 are sized to span between the openings 120, 122, 124 and vent ports 126, 128 in order to connect the various flow paths. Specifically, the indentation 136 is sized to span between the vent port 126 and the opening 124, and between the opening 124 and the opening 122. The indentation 138 is sized to span between the opening 122 and the opening 120, and between the opening 120 and the vent port 128.

Referring to both FIGS. 6 and 7, the complete operation of the device 10 is apparent. Before activation, in FIG. 6, the medication flow path 44 is interrupted by the liquid seal 140 on the valve 18 to prevent flow of medication to the needle. The second pressure flow path 150 to the lower inlet 91 is open, so that air pressure within that flow path lifts the piston 30 and retains it in the retracted position, with the needle 34 safely housed inside the device 10. The upper vent path 154 is open, allowing the air above the piston plate 104 to vent, so that air is not trapped above the piston to prevent the piston from moving up into the retracted position. The third pressure flow path 152 from the pressure housing 28 to the upper inlet 92 is closed, so that no pressure flows to the top surface 105 of the piston plate 104 to move the piston downwardly. The lower vent path 156 is also closed, so that the air pressure under the piston plate 104 does not vent, causing the piston 30 to slide down.

In this state, the piston 30 and attached needle 34 are stored in the raised position, and the liquid medication is sealed. The device 10 can be shipped, stored, and carried by the user until ready for use. The device can be stored in various orientations, and the wide liquid seal 140 prevents the liquid from flowing to the needle before the device is ready for use. If the piston 30 is inadvertently pushed down during shipment, the air inside the chamber 84 below the piston plate 104 will exert pressure back on the piston to retain it into the retracted position. The air inside the chamber 84 under the piston plate 104 is sealed (by the seal 108 at one end and the pressure housing at the other), so that the air does not leak out and allow the piston to slide downwardly. Because there are no vent paths available to this air, the air acts as a cushion to retain the piston 30 in the raised position during shipment and storage.

When the user is ready to use the device 10 to inject the medication, the user first removes a cover sheet or liner 11 (see FIG. 1) from the bottom surface of the base 14 to expose an adhesive layer along the bottom surface of the base 14. The user presses this adhesive surface against the skin at the desired location of the injection. The hole 110 in the base 14 indicates exactly where the needle will extend to insert into the skin. The user can align this hole 110 with the desired point of injection on the skin.

The user then presses the activation button 20 to generate the gas pressure inside the device. As explained above, the button 20 moves downwardly into the pressure housing 28 and causes the two chemical reactants 70, 72 to contact each other, thereby initiating the chemical reaction that generates the gas pressure. At this point, the valve 18 remains in the "stop" position shown in FIG. 6. As a result, while the gas pressure builds in the pressure housing 28, the medication flow path 44 remains closed, and the third pressure flow path 152 remains closed. The gas pressure from the pressure housing flows through the first pressure flow path 40 into the medication reservoir 24 and pushes the medication along the medication flow path 44 to the seal 140, where it is prevented from flowing any further. Also, pressure from the pressure housing 28 flows through the open second pressure flow path 150 to the lower inlet 91 and into the chamber 84 below the piston plate 104. This pressure further retains the piston in the raised, retracted position.

When the user is ready for the injection, he or she presses the start button 130 on the spool 112. The start and stop buttons on the spool are accessible through windows 16a and 16b on the cover 12 (see FIG. 1), so the user can push the buttons to slide the spool 112 in the valve. When the user presses the start button 130, the spool 112 translates within the valve housing 114 to the start position shown in FIG. 7. As described above, this movement of the spool 112 opens the medication flow path 44 (through groove 142), opens the third pressure flow path 152 to the upper inlet 92, and opens the lower vent path 156. This movement also closes the second pressure flow path 150 and closes the upper vent path 154. As a result, gas pressure from the pressure housing now flows through the third flow path 152 into the chamber 84, where it presses on the top surface 105 of the plate 104. The air in the chamber 84 below the piston plate 104 vents to the atmosphere through the lower vent path 156. The pressure on the top side 105 of the piston plate 104 and the open vent path on the bottom side of the piston plate 104 cause the piston plate 104 to move downwardly through the chamber 84 to the deployed position (shown in FIG. 4C). The needle 34 moves with the piston and extends through the opening 110 into the user's skin. At the same time, the gas pressure flowing through the first pressure flow path 40 pushes on the flexible membrane 60 inside the medication reservoir, and the medication flows through the flow path 44 to the needle 34 and to the user.

Thus, when the user presses the start button, the needle automatically inserts and the medication automatically flows through the needle and to the user for sub-cutaneous injection. The gas pressure flow through the third pressure flow path 152 more quickly than the medication flows through the medication flow path 44, and therefore the needle 34 is inserted before the medication reaches the needle, so that no medication is lost.

When the medication has been fully delivered, or earlier if the user desires, the user presses the stop button 132. The movement of the stop button 132 returns the spool 112 to the stop position shown in FIG. 6. This movement brings the seal 140 between the inlet 48a and outlet 48b on the valve housing 114, closing the medication flow path 44 and blocking any further flow of medication if not already completely delivered. The third pressure flow path 152 and lower vent path 156 are closed, and the second pressure flow path 150 and upper vent path 154 are opened. As a result, the gas pressure above the piston plate 104 is vented, and the gas pressure is routed through the inlet 91 below the piston plate 104, thereby raising the piston 30. Thus when the stop button 132 is pressed, the needle 34 automatically retracts into the device 10. The pressurized chamber 84 below the piston plate 104 retains the needle 34 within the device 10 for safe disposal. In one embodiment the device 10 is a one-time use device that is discarded after the medication is delivered and the needle safely retracted within the device.

In the cycle of operation of the device 10 as just described, the device alternates pressure and vent paths on opposite sides of the piston 30 to advance and retract the needle. That is, in one position of the valve 18, a first side of the piston 30 (the upwardly facing surface 105) is vented and the opposite side (the downwardly facing surface 107) is pressurized. When the valve is moved to the second position, the pressure and vent paths are reversed, such that the first side of the piston is pressurized, and the opposite side is vented. The alternating pressure and vent paths through the valve enable the piston and needle to be alternately advanced and retracted.

Figure 8:
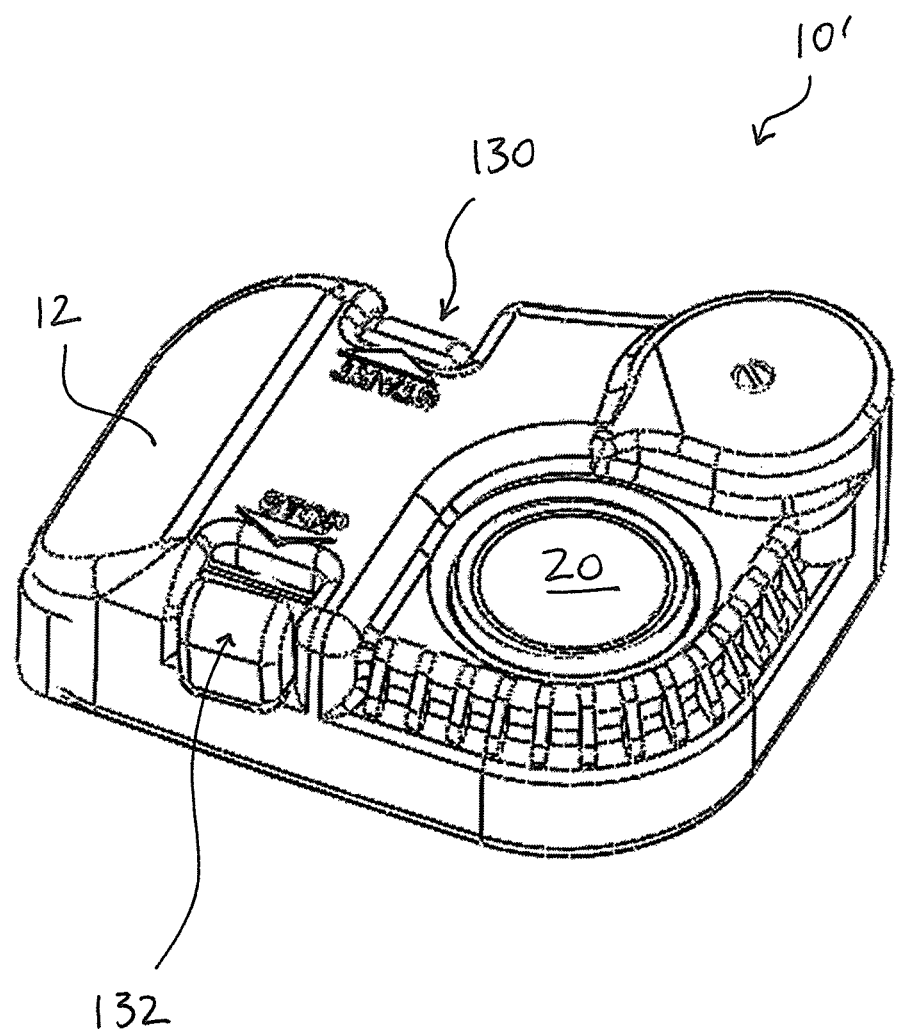
FIG. 8 is a perspective view of a medication delivery device according to another embodiment of the invention.

An embodiment of a medication delivery device 10' is shown in FIG. 8. The device 10' operates in the same way described above. The device includes a cover 12, activation button 20, and start and stop buttons 130, 132. The user presses the activation button 20 to activate a chemical reaction or otherwise release the gas pressure inside a pressure housing within the device. The user presses the start button 130 to move a valve to the start position, to deploy the needle and allow the flow of medication to the needle. The user presses the stop button 132 to move the valve to the stop position to retract the needle and prevent further flow of medication. The device 10' is packaged compactly inside the cover 12, so that it is portable and convenient for the user to carry. The three buttons 20, 130, 132 extending from the cover 12 are easy to operate, and the instructions for use are clear. Thus the patient can safely and easily administer the medication without complex instructions or preparations, and can safely dispose of the needle 34 after injection. The user can administer the medication at any desired location without the assistance of a medical professional.

In one embodiment, the device 10' is approximately 1 inch in height, 2.75 inches in length, and 2.65 inches in width.

Although the present invention has been described and illustrated in respect to exemplary embodiments, it is to be understood that it is not to be so limited, and changes and modifications may be made therein which are within the full intended scope of this invention as hereinafter claimed. For example, while screws 54 are shown for assembly of the medication reservoir, and for attachment of the lid 86 to the piston housing 32, other types of fasteners can be used, including mechanical fasteners and/or adhesives, or ultrasonic welding of the plastic components, or other fastening methods. The medication reservoir 24 may be integrally as one continuous piece rather than two separate components attached together. Additionally, the base 14 can be used as a part of various components, such as the fill port 65 or the bottom portion of the medication reservoir or the piston assembly 26, but in alternative embodiments these features can be provided separately from the base 14 and can be mounted to the base.

The source of gas pressure is described above as carbon dioxide byproduct from a reaction of citric acid and calcium carbonate, but other sources of gas pressure may be used. For example, the gas pressure can be generated from other chemical reactants such as other acids and metal carbonates, such as acetic acid and sodium or magnesium carbonate, or other acid solutions and alkali metal carbonates. Additional examples of acids, carbonates, and other reactants can be found in U.S. Pat. No. 5,700,245, the contents of which are incorporated herein by reference. The gas pressure can be contained within a pre-pressurized gas canister which is punctured by the activation button to release the pressure.

The valve 18 above is a spool-type valve, but in other embodiments the valve has other structures, such as a screw valve, a rotary valve or other types of valves.

The tubes 50a, 50b that form part of the medication flow path 44 can be chosen according to the particular medication being dispensed, in order to provide a flow path with the desired cross-sectional area depending on the medication's viscosity and volume. The length and inner diameter of the tubing can be chosen to alter the rate of flow of the medication through the tube to provide the desired rate of delivery into the skin. The needle 34 can likewise be chosen based on the medication and the depth, volume, and rate of injection.

Additional features may be included with the device 10 even though they are not shown here. For example, an additional safety mechanism such as a pin may be utilized to retain the needle in the retracted position during shipment, prior to use. The user can remove the pin from the device to release the needle prior to use. Another safety mechanism such as a latch can be activated after use to retain the used needle in the retracted position for disposal. Another option is a spring-loaded sheath that covers the needle when the needle is removed from the body. A window may be provided in the cover 12 to view the medication reservoir 24 so that the user can see when the medication is fully exhausted from the reservoir and the injection is complete. Other indications that the injection is complete may be provided, such as a paddle wheel that provides an audible click when the medication reservoir is empty. Alternatively, a tactile indicator triggered by a position sensor could be provided for the completion of the injection.

Some features described above may be omitted in other embodiments. For example, when the medication is inserted into the reservoir 24 in a sealed flexible bag, the flexible membrane 60 may be omitted. Gas pressure from the first pressure flow path 40 presses directly on the bag to cause the medication to flow, rather than pushing on the membrane 60.

These are just a few examples of the many alternative designs and modifications that may be provided without departing from the scope of the invention.

What is claimed is:

1. A medication delivery device for injection of a medication, comprising:
    a medication reservoir;
    a pressure housing;
    a piston assembly comprising a piston coupled to a needle, the piston being movable from a retracted position to a deployed position; and
    a valve fluidically coupled between the medication reservoir and the needle and between the pressure housing and the piston assembly,
    wherein the valve is movable from a first position in which the pressure housing is fluidically coupled to the piston assembly through a first fluid flow path, to a second position in which the pressure housing is fluidically coupled to the piston assembly through a second fluid flow path.

2. The medication delivery device of claim 1, wherein the first fluid flow path is fluidically coupled to a first side of the piston, and the second fluid flow path is fluidically coupled to a second side of the piston that is opposite the first side.

3. The medication delivery device of claim 2, wherein the first side of the piston comprises a downwardly facing surface, and the second side of the piston comprises an upwardly facing surface.

4. The medication delivery device of claim 3, wherein the piston comprises a plate having the upwardly and downwardly facing surfaces, and wherein the plate is slidable within a piston housing to move the piston from the retracted position to the deployed position.

5. The medication delivery device of claim 1, further comprising a third fluid flow path from the pressure housing to the medication reservoir.

6. The medication delivery device of claim 5, further comprising a medication flow path from the medication reservoir to the needle.

7. The medication delivery device of claim 6, wherein the valve comprises a seal that is positioned to block the medication flow path when the valve is in the first position and a passage that is positioned to align with the medication flow path when the valve is in the second position.

8. The medication delivery device of claim 6, further comprising a first vent path fluidically coupling the piston assembly to a first vent port and a second vent path fluidically coupling the piston assembly to a second vent port.

9. The medication delivery device of claim 8, wherein the valve comprises a first indentation that aligns with the first vent path in the first position of the valve and aligns with the second flow path in the second position of the valve, and wherein the valve comprises a second indentation that aligns with the first flow path in the first position of the valve and aligns with the second vent path in the second position of the valve.

10. The medication delivery device of claim 9, wherein the valve further comprises a second seal that is positioned to block the first vent path in the second position of the valve, and a third seal that is positioned to block the second flow path in the first position of the valve and is positioned to block the first flow path in the second position of the valve, and a fourth seal that is positioned to block the second vent path in the first position of the valve.

11. A medication delivery device for injection of a medication, comprising:
   a medication reservoir;
   a pressure housing containing a source of gas pressure;
   a piston assembly comprising a piston coupled to a needle, the piston being movable from a retracted position to a deployed position;
   a first flow path from the pressure housing to the piston assembly;
   a medication flow path from the medication reservoir to the needle; and
   a valve fluidically coupled between the pressure housing and the piston assembly, the valve being movable from a first position in which the valve blocks a flow of the gas pressure through the first flow path, to a second position in which the valve allows such flow to move the piston assembly from the retracted position to the deployed position, and wherein the valve comprises a seal that blocks the medication flow path in the first position of the valve, and wherein the valve comprises a passage that aligns with the medication flow path in the second position of the valve.

12. The medication delivery device of claim 11, further comprising a second flow path from the pressure housing to the piston assembly, wherein in the first position the valve allows a flow of the gas pressure through the second flow path to move the piston assembly to the retracted position, and in the second position the valve blocks such flow through the second flow path.

13. The medication delivery device of claim 12, wherein the first flow path is fluidically coupled to an upwardly facing surface of the piston assembly, and wherein the second flow path is fluidically coupled to a downwardly facing surface of the piston assembly.

14. The medication delivery device of claim 12, further comprising a third pressure flow path from the pressure housing to the medication reservoir.

15. The medication delivery device of claim 11, further comprising an activation button attached to the pressure housing for releasing the gas pressure from the pressure housing.

16. A medication delivery device for injection of a medication, comprising:
   a medication reservoir;
   a source of gas pressure;
   a piston assembly comprising a piston coupled to a needle;
   a valve configured to regulate a first fluid flow path from the source of gas pressure to the medication reservoir, and a second fluid flow path from the source of gas pressure to the piston assembly;
   wherein the needle is fluidically coupled to the medication reservoir by the valve, and
   wherein the piston is movable, by a fluid flow from the source of gas pressure, from a retracted position in which the needle is contained within the medication delivery device to a deployed position in which the needle extends from the medication delivery device, and is movable, by the fluid flow from the source of gas pressure, from the deployed position to the retracted position.

17. The medication delivery device of claim 16, further comprising a valve fluidically coupled between the source of gas pressure and the piston assembly, the valve being movable from a first position in which the valve fluidically connects the fluid flow from the source of gas pressure to a first side of the piston to move the piston to the retracted position, to a second position in which the valve fluidically connects the fluid flow from the source of gas pressure to a second opposite side of the piston to move the piston from the retracted position to the deployed position, and back to the first position to move the piston from the deployed position to the retracted position.

18. The medication delivery device of claim 17, wherein the valve comprises a spool valve having a plurality of passages and a plurality of seals for allowing and blocking the fluid flow from the source of gas pressure.

19. A method for injecting medication, comprising:
   providing a medication delivery device comprising:
      a medication reservoir containing a medication;
      a pressure housing containing a source of gas pressure;
      a piston assembly comprising a piston coupled to a needle, the piston being movable from a retracted position in which the needle is contained within the medication delivery device to a deployed position in which the needle extends from the medication delivery device; and
   a valve fluidly coupled between the medication reservoir and the needle and between the pressure housing and the piston assembly;
   deploying the needle by communicating a fluid flow from the source of gas pressure to the piston assembly;
   delivering the medication to the needle by communicating the fluid flow from the source of gas pressure to the medication reservoir; and
   retracting the needle by communicating the fluid flow from the source of gas pressure to the piston assembly.

20. The method of claim 19, wherein deploying the needle comprises communicating the fluid flow from the source of gas pressure to an upwardly facing surface of the piston, and wherein retracting the needle comprises communicating the fluid flow from the source of gas pressure to an opposite, downwardly facing surface of the piston.

* * * * *